United States Patent
Fu et al.

(10) Patent No.: US 12,030,961 B2
(45) Date of Patent: Jul. 9, 2024

(54) METHOD FOR REMOVING ORGANIC SOLVENT FROM STARCH HEMOSTATIC MICROSPHERES

(71) Applicant: Hangzhou Singclean Medical Products Co., Ltd, Zhejiang (CN)

(72) Inventors: Yang Fu, Zhejiang (CN); Jie Li, Zhejiang (CN); Zhongyi Chen, Zhejiang (CN)

(73) Assignee: Hangzhou Singclean Medical Products Co., Ltd, Hangzhou (CN)

( * ) Notice: Subject to any disclaimer, the term of this patent is extended or adjusted under 35 U.S.C. 154(b) by 446 days.

(21) Appl. No.: 17/479,586

(22) Filed: Sep. 20, 2021

(65) Prior Publication Data
US 2022/0204652 A1 Jun. 30, 2022

(30) Foreign Application Priority Data
Dec. 24, 2020 (CN) .......................... 202011547512.1

(51) Int. Cl.
*C08B 30/06* (2006.01)
*A61L 15/28* (2006.01)
(Continued)

(52) U.S. Cl.
CPC .............. *C08B 30/06* (2013.01); *A61L 15/28* (2013.01); *A61L 15/42* (2013.01);
(Continued)

(58) Field of Classification Search
CPC .... A61L 24/0042; A61L 24/001; A61L 24/08; A61L 15/28; A61L 15/42; A61L 15/62;
(Continued)

(56) References Cited

U.S. PATENT DOCUMENTS

| | | | | |
|---|---|---|---|---|
| 2,764,159 A | * | 9/1956 | Masci | ..................... A61L 15/64 604/375 |
| 2,914,444 A | * | 11/1959 | Smith | ..................... A61L 15/28 536/87 |

(Continued)

FOREIGN PATENT DOCUMENTS

| | | | | |
|---|---|---|---|---|
| CA | 2846682 A1 | * | 3/2013 | ....... A61F 13/00063 |
| CN | 102406956 B | | 9/2013 | |

(Continued)

OTHER PUBLICATIONS

English Translation of Patent Publication CN101049513B, published May 2010. (Year: 2010).*
English Translation of Patent Publication CN205434088U, published Aug. 2016. (Year: 2016).*
English Translation of Patent Publication WO 2019011333A1, published Jan. 2019. (Year: 2019).*

*Primary Examiner* — Joseph W Drodge

(57) ABSTRACT

The present invention provides a method for removing an organic solvent from starch hemostatic microspheres, comprising the following steps: 1. taking to-be-dried starch hemostatic microspheres and laying them flatly on drying trays with attention to laying them as uniformly and thinly as possible; 2. taking an adsorbent and subpackaging it into dialyzing paper bags for sealing; and 3. placing the trays and the dialyzing paper bags completed in the previous two steps on separators of a low-temperature vacuum oven in layers, setting the oven temperature at 0-20° C., then vacuumizing and keeping pressure for 15-48 hours. The method provided by the present invention can reduce organic solvent residue in the starch hemostatic microspheres to less than 0.05%, which meets the requirements of relevant standards for medical devices, thereby improving safety of products.

2 Claims, 2 Drawing Sheets

(51) Int. Cl.
  *A61L 15/42* (2006.01)
  *B01D 53/04* (2006.01)
  *F26B 7/00* (2006.01)
(52) U.S. Cl.
  CPC ............ *B01D 53/0407* (2013.01); *F26B 7/00* (2013.01); *A61L 2400/04* (2013.01); *B01D 2253/202* (2013.01)
(58) Field of Classification Search
  CPC ..... A61L 2400/04; C08B 30/00; C08B 30/06; F26B 5/04; F26B 5/045; F26B 7/00; C08L 3/02; C08L 3/04; B01D 2253/202; B01D 2253/102; B01D 53/0407; B01D 2253/108; B01D 2253/11; B01D 2253/204; B01D 2257/70; B01D 2257/80; B01D 2259/4541
  See application file for complete search history.

(56) References Cited

U.S. PATENT DOCUMENTS

2007/0154509 A1* 7/2007 Wilcher .............. A61F 13/0206
                                                      424/422
2009/0123525 A1* 5/2009 Bedard ................ A61K 45/06
                                                      424/443
2018/0179301 A1* 6/2018 Zhang .................... C08B 31/18

FOREIGN PATENT DOCUMENTS

CN      205434088 U  *  8/2016  ............ A61F 13/02
GB          750325 A  *  6/1956
WO  WO-2019011333 A1  *  1/2019  ............ A61L 15/28

* cited by examiner

ID#:1  Name: Ethanol f(x)=2.18847294885e-003*x+12.842484217
R=0.996936905714  R^2=0.993883193975
External Standard

| No. | Conc. | Area |
|---|---|---|
| 1 | 23.60 | 7199 |
| 2 | 47.20 | 16333 |
| 3 | 141.60 | 53295 |
| 4 | 188.80 | 80624 |
| 5 | 236.00 | 104370 |

Calibration Curve - Analytical Line 1 - Channel 1

ID#:2  Name: Ethyl acetate f(x)=6.62382713417e-004*x+18.3252025928
R=0.996181470784  R^2=0.992377522732
External Standard

| No. | Conc. | Area |
|---|---|---|
| 1 | 24.68 | 19032 |
| 2 | 49.36 | 41594 |
| 3 | 148.08 | 183288 |
| 4 | 197.44 | 278835 |

METHOD FOR REMOVING ORGANIC SOLVENT FROM STARCH HEMOSTATIC MICROSPHERES

CROSS REFERENCE TO RELATED APPLICATIONS

This application claims priority to Chinese Patent Application No. 202011547512.1 filed on Dec. 24, 2020, the entire contents of which are incorporated herein by reference.

FIELD OF THE INVENTION

The present invention relates to a method for removing an organic solvent from starch hemostatic microspheres, and belongs to the field of medical devices.

BACKGROUND OF THE INVENTION

Starch hemostatic microspheres are absorbable and implantable medical devices prepared from starch. In production of products, a prepared starch solution needs to be made into microsphere particles through emulsification, crosslinking and other technologies, and at the later period of production, a crosslinking agent, an emulsifier and the like in a system should be removed. Due to the hydroscopicity of the prepared microsphere particles, they cannot be washed with water, instead, they need to be washed with organic solvents, which is helpful for removing water from the particles at the same time. Thus, the organic solvents are inevitably used in the production process of this product, and if the drying method is not appropriate, excessive solvent residue may exist in the product. Solvent residue is a non-negligible problem in the products of pharmaceutical industry, especially for implantable-grade medical devices, and solvents in the products penetrate into a human body through tissue fluid, which may cause inflammatory responses of human tissues or even poisoning. Therefore, manufacturers need to ensure the biosafety of the products for use in human bodies by developing an appropriate process to remove the solvent residue to a safety limit. Generally, the standards for the solvent residue of the medical devices can refer to the requirements of *Pharmacopoeia of the People's Republic of China* (hereinafter referred to as the Pharmacopoeia). In 0861 Residual Solvents Determination Method of Pharmacopoeia Volume III, residue limits of common solvents in drugs are specified, for instance, the limit value of class III solvents (i.e. Usage limited by drug GMP and other quality requirements) such as ethyl alcohol and ethyl acetate is 0.5%. The limit value is the minimum requirement of the solvent residue limits of the products.

For the starch hemostatic microsphere product, common solvent removal methods include vacuum drying, spray drying, forced air drying and freeze drying. For example, in invention patent CN102406956B-starch hemostatic microspheres and preparation method thereof, it discloses microspheres being formed through spray drying after being washed. In these methods, except for the freeze drying, the rest all remove the organic solvent through a high-temperature volatilization or high-temperature plus low-pressure volatilization principle, and the organic solvent used by the starch hemostatic microspheres is usually low-boiling ethyl acetate, ethyl alcohol, etc., thus, the solvent on the surfaces of the microspheres often can be rapidly volatilized at high temperature, while the solvent inside the microspheres is wrapped by the surface and cannot be removed. In this case, the residual solvent can be removed by further increasing the temperature to change the surface structure of the microspheres, which is prone to causing yellowing and denaturation of the product and a large energy loss. In contrast, the above defects can be avoided through solvent sublimation-condensation freeze drying at low temperature, which seems to be a reasonable method. However, the melting points of the organic solvents are very low, for example, the melting point of ethanol is about-114° C., which requires a lot of energy to complete freezing of the ethyl alcohol, thereby causing excessive energy consumption. Thus, freeze drying is also not suitable for the removal of the organic solvents in industrial production.

SUMMARY OF THE INVENTION

In view of the defects of existing technical methods, the present invention provides a method for removing an organic solvent from starch hemostatic microspheres.

In order to achieve the above purposes, the present invention is realized through such a technical solution that:

A method for removing the organic solvent from the starch hemostatic microspheres comprises the following preparation steps:

(1) taking to-be-dried starch hemostatic microspheres and laying them flatly on drying trays with attention to laying them as uniformly and thinly as possible;

(2) taking an adsorbent according to a mass ratio of 20%-100% of a to-be-dried product and subpackaging the adsorbent into dialyzing paper bags for sealing; and (3) placing the trays loaded with the starch hemostatic microspheres and the dialyzing paper bags loaded with the adsorbent on separators of a low-temperature vacuum oven in layers, setting the oven temperature at 0-20° C., then vacuumizing, and keeping pressure for 15-48 hours.

Further, in step (2), the adsorbent is a dry solid, which has a physical adsorption function on organic gases, and mainly acts on adsorption of the organic gases volatilized from the starch hemostatic microspheres.

Preferably, the adsorbent is one or more selected from activated carbon, molecular sieve, clay, metal-organic frameworks (MOFs) and polymeric adsorbent resin.

Preferably, in step (2), the adsorbent is the inexpensive activated carbon or molecular sieve.

The method steps adopted by the present invention are designed based on a low-boiling solvent commonly used in production and processing of the starch hemostatic microspheres. The present invention enables the solvent in the starch hemostatic microspheres to be gradually and slowly volatilized by way of low temperature and negative pressure. In this way, the solvent in the starch hemostatic microspheres can be completely volatilized, thereby avoiding the situation that the solvent on surfaces of the microspheres are rapidly volatilized at high temperature, while the solvent inside the microspheres is wrapped and cannot be released. In the meantime, the present invention enables the volatilized organic gases to be absorbed by the adsorbent so as to reduce the equilibrium pressure of the organic gases in a negative-pressure sealed system, thereby making complete volatilization of the organic solvent in the microspheres.

The dialyzing paper bags with a gas penetration function are also adopted by the present invention to seal the adsorbent and placed in layers with the starch hemostatic microspheres in the oven, so as to avoid cross pollution caused by the contact between the adsorbent and the starch hemostatic microspheres when effective adsorption of the organic gases is ensured.

The beneficial effects of the present invention are as follows. The method for removing the organic solvent from the starch hemostatic microspheres is provided. The present invention can effectively remove the low-boiling solvent (i.e. ethyl alcohol and ethyl acetate) commonly used in production and processing of the starch hemostatic microspheres. By the implementation of the present invention, solvent residue in the starch hemostatic microspheres can be reduced to less than 0.05% (the testing method: taking a solution for gas chromatograph (GC) after enzymolysis of the microspheres), which is far below the limits required by Pharmacopoeia, thereby improving the safety of the starch hemostatic microspheres. Table 1 shows the comparison between the effect of the present invention and the effect of a common high-temperature vacuum drying method on removal of the ethyl alcohol and the ethyl acetate from the starch hemostatic microspheres. As can be seen from data of the table, the solvent removal effect of the present invention is far superior to that of the common high-temperature vacuum drying method. Moreover, the method of the present invention basically has no influence on the water absorption of the product and the initial amount of contaminated bacteria, thereby not changing product performance.

TABLE 1

Comparison of testing results of different drying methods for starch hemostatic microspheres

| Test items | Drying methods for starch hemostatic microspheres | |
| --- | --- | --- |
| | Method of present invention [Note1] | High-temperature vacuum drying method [Note2] |
| Ethyl alcohol residue | 0.030% | 2.18% |
| Ethyl acetate residue | 0.020% | 1.02% |
| Water absorption of product | 1304% | 1280% |
| Initial amount of contaminated bacteria | ≤10 cfu/g | ≤10 cfu/g |

[Note1] according to a method of Embodiment 1.
[Note2] according to a method of sample NO. 2 of Embodiment 6.

BRIEF DESCRIPTION OF DRAWINGS

in FIG. 1: 1. Low-temperature vacuum oven, 2. Oven body, 3. Separators, 4. Trays placed in layers for to-be-dried samples, and 5. Dialyzing paper bags placed in layers and loaded with adsorbents.

DETAILED DESCRIPTION

The substantive features and notable progress of the present invention are further clarified by introducing embodiments of the present invention, but the present invention is by no means limited to the embodiments.

Embodiment 1

Figure 1:
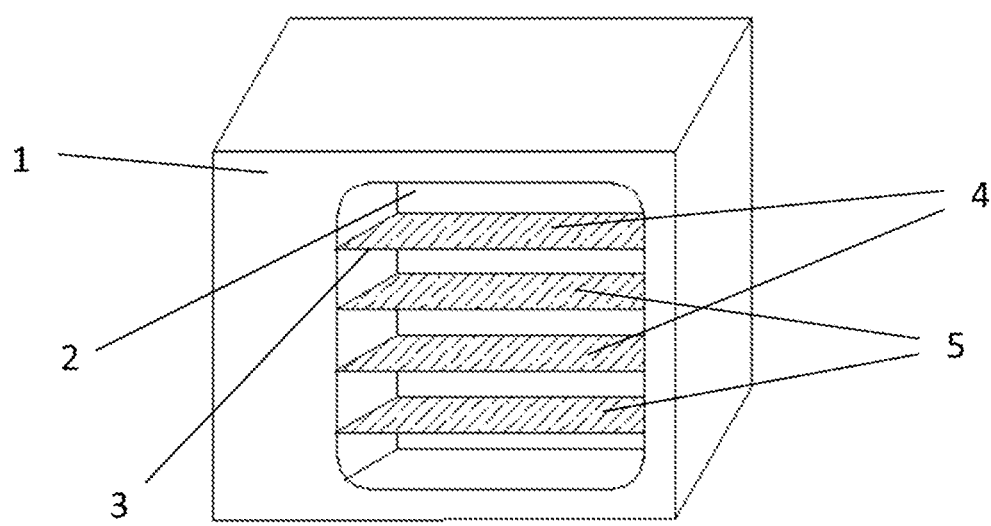
FIG. 1 is a schematic diagram of embodiments of the present invention.

(1) To-be-dried starch hemostatic microspheres were taken and laid flatly on drying trays with attention to laying them as uniformly and thinly as possible;

(2) activated carbon particles were taken according to a mass ratio of 55% of a to-be-dried product and subpackaged into dialyzing paper bags to be sealed; and (3) as shown in FIG. 1, the trays loaded with the starch hemostatic microspheres and the dialyzing paper bags loaded with an adsorbent were placed on separators 3 in an oven body 2 of a low-temperature vacuum oven 1 in layers, after placing, the positions were as shown in 4 and 5, an oven door was closed, the temperature of the oven 1 was set at 12° C., then vacuumizing was conducted to −0.08 MPa, and the pressure was kept for 24 hours.

Figure 2:
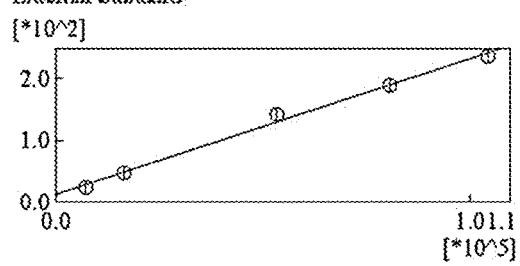
FIG. 2 shows GC testing results of residual ethyl alcohol and ethyl acetate in starch hemostatic microspheres treated by Embodiment 1 of the present invention.
Figure 2:
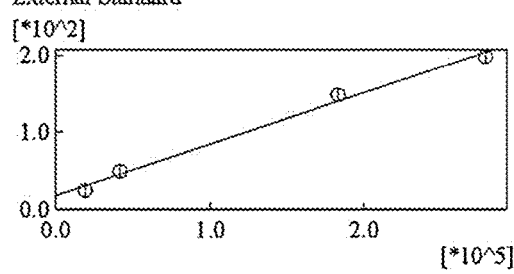
Figure 2:
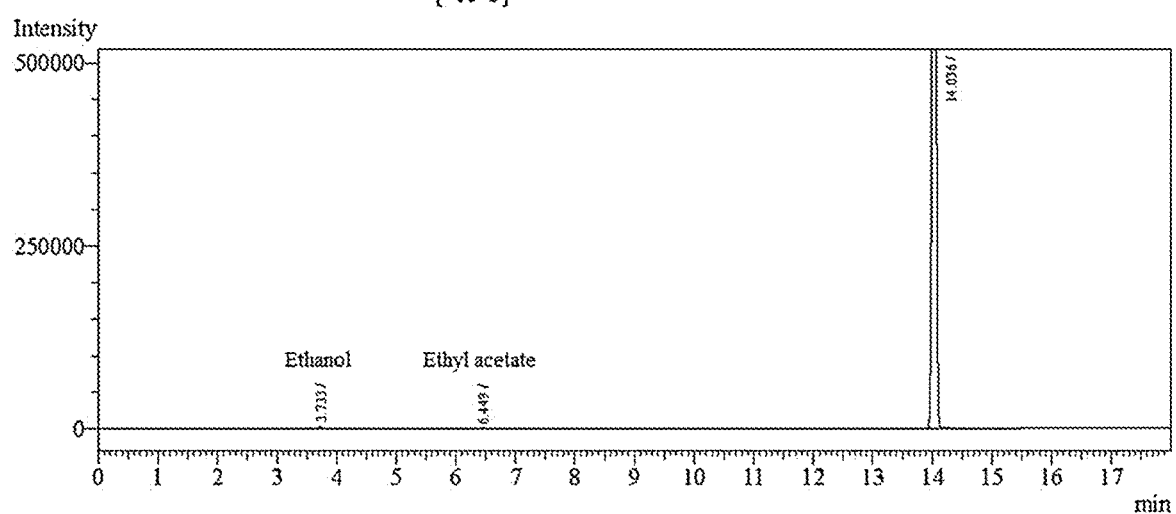

After the product was taken to be subjected to enzymolysis with amylase in purified water, the content of ethyl alcohol and ethyl acetate in the starch hemostatic microspheres was tested through a GC method, as shown in FIG. 2, wherein data were shown in the following table.

| Sample preparation | 0.5018 g starch hemostatic microspheres in 5.0 mL purified water | | |
| --- | --- | --- | --- |
| Ret. time of ethyl alcohol | 3.733 | Ret. time of ethyl acetate | 6.449 |
| Area of ethyl alcohol | 9226 | Area of ethyl acetate | 3994 |
| Content of ethyl alcohol | 0.030% | Content of ethyl acetate | 0.020% |

Embodiment 2

(1) An appropriate number of to-be-dried starch hemostatic microspheres were taken and laid flatly on drying trays with attention to laying them as uniformly and thinly as possible;

(2) a 4A molecular sieve was taken according to a mass ratio of 60% of a to-be-dried product and subpackaged into dialyzing paper bags to be sealed; and (3) as shown in FIG. 1, the trays loaded with the starch hemostatic microspheres and the dialyzing paper bags loaded with an adsorbent were placed on separators 3 in an oven body 2 of a low-temperature vacuum oven 1 in layers, after placing, the positions were as shown in 4 and 5, an oven door was closed, the temperature of the oven 1 was set at 20° C., then vacuumizing was conducted to −0.05 MPa, and the pressure was kept for 15 hours.

After the product was taken to be subjected to enzymolysis with amylase in purified water, the content of ethyl alcohol and ethyl acetate in the starch hemostatic microspheres was tested through a GC method, as shown in the following table.

| | |
| --- | --- |
| Content of ethyl alcohol | 0.008% |
| Content of ethyl acetate | 0.009% |

Embodiment 3

(1) An appropriate number of to-be-dried starch hemostatic microspheres were taken and laid flatly on drying trays with attention to laying them as uniformly and thinly as possible;

(2) clay was taken according to a mass ratio of 100% of a to-be-dried product and subpackaged into dialyzing paper bags to be sealed; and (3) as shown in FIG. 1, the trays loaded with the starch hemostatic microspheres and the dialyzing paper bags loaded with an adsorbent were placed on separators 3 in an oven body 2 of a low-temperature vacuum oven 1 in layers, after placing, the positions were as shown in 4 and 5, an oven door was closed, the temperature of the oven was set at 0° C., then vacuumizing was conducted to −0.1 MPa, and the pressure was kept for 48 hours.

After the product was taken to be subjected to enzymolysis with amylase in purified water, the content of ethyl alcohol and ethyl acetate in the starch hemostatic microspheres was tested through a GC method, as shown in the following table.

| | |
|---|---|
| Content of ethyl alcohol | 0.006% |
| Content of ethyl acetate | 0.010% |

Embodiment 4

(1) An appropriate number of to-be-dried starch hemostatic microspheres were taken and laid flatly on drying trays with attention to laying them as uniformly and thinly as possible;

(2) metal-organic frameworks (MOFs) were taken according to a mass ratio of 20% of a to-be-dried product and subpackaged into dialyzing paper bags to be sealed; and (3) as shown in FIG. 1, the trays loaded with the starch hemostatic microspheres and the dialyzing paper bags loaded with an adsorbent were placed on separators 3 in an oven body 2 of a low-temperature vacuum oven 1 in layers, after placing, the positions were as shown in 4 and 5, an oven door was closed, the temperature of the oven was set at 0° C., then vacuumizing was conducted to −0.1 MPa, and the pressure was kept for 48 hours.

After the product was taken to be subjected to enzymolysis with amylase in purified water, the content of ethyl alcohol and ethyl acetate in the starch hemostatic microspheres was tested through a GC method, as shown below.

| | |
|---|---|
| Content of ethyl alcohol | 0.020% |
| Content of ethyl acetate | 0.008% |

Embodiment 5

(1) An appropriate number of to-be-dried starch hemostatic microspheres were taken and laid flatly on drying trays with attention to laying them as uniformly and thinly as possible;

(2) polymeric adsorbent resin was taken according to a mass ratio of 50% of a to-be-dried product and subpackaged into dialyzing paper bags to be sealed; and (3) as shown in FIG. 1, the trays loaded with the starch hemostatic microspheres and the dialyzing paper bags loaded with an adsorbent were placed on separators 3 in an oven body 2 of a low-temperature vacuum oven 1 in layers, after placing, the positions were as shown in 4 and 5 an oven door was closed, the temperature of the oven was set at 0° C., then vacuumizing was conducted to −0.1 MPa, and the pressure was kept for 48 hours.

After the product was taken to be subjected to enzymolysis with amylase in purified water, the content of ethyl alcohol and ethyl acetate in the starch hemostatic microspheres was tested through a GC method, as shown below.

| | |
|---|---|
| Content of ethyl alcohol | 0.023% |
| Content of ethyl acetate | 0.008% |

Embodiment 6

(1) Starch hemostatic microspheres were taken according to the method of Embodiment 1 to be dried, and this batch was marked as NO.1;

(2) the same number of to-be-dried starch hemostatic microspheres were taken and uniformly and thinly laid on drying trays flatly, and this batch was marked as NO.2; and (3) the trays loaded with sample NO.2 were placed in a common vacuum oven, the oven temperature was set at 70° C., a vacuum was set to be −0.1 MPa, and the pressure was kept for 24 hours.

Testing: after sample NO.1 and sample NO.2 were taken respectively to be subjected to enzymolysis with amylase in purified water, the content of ethyl alcohol and ethyl acetate in the product was tested respectively through a GC method; the water absorption of sample NO.1 and sample NO.2 was measured by respectively weighing their mass before and after water absorption at saturation; and the initial amount of contaminated bacteria of the samples was detected by 1100 Microbiological Tests of General Requirements of Pharmacopeia Volume IV, and results were as follows.

| Test items | Sample NO. 1 | Sample NO. 2 |
|---|---|---|
| Ethyl alcohol residue | 0.030% | 2.18% |
| Ethyl acetate residue | 0.020% | 1.02% |
| water absorption | 1304% | 1280% |
| Initial amount of contaminated bacteria | ≤10 cfu/g | ≤10 cfu/g |

The invention claimed is:

1. A method for removing an organic solvent from starch hemostatic microspheres, comprising the following steps:
   (1) laying the starch hemostatic microspheres flatly on drying trays;
   (2) taking an adsorbent according to a mass ratio of 20% to 100% of the starch hemostatic microspheres, packaging the adsorbent into dialyzing paper bags, and sealing the dialyzing paper bags, wherein the adsorbent is an adsorbent capable of adsorbing organic gases contained in the starch hemostatic microspheres; and
   (3) placing the drying trays loaded with the starch hemostatic microspheres obtained in step (1) and the sealed dialyzing paper bags obtained in step (2) within a low-temperature vacuum oven in layers, setting the oven temperature at 0-20° C., then vacuumizing the oven to a negative pressure of −0.1 to −0.05 MPa, and keeping the pressure of −0.1 to −0.05 MPa within the oven for 15-48 hours.

2. The method for removing the organic solvent from the starch hemostatic microspheres according to claim 1, wherein the adsorbent is a solid selected from the group consisting of activated carbon, molecular sieve, clay, metal-organic frameworks (MOFs) and polymeric adsorbent resin.

* * * * *